United States Patent [19]

Hukuba

[11] Patent Number: 5,406,664
[45] Date of Patent: Apr. 18, 1995

[54] TOOTHBRUSH

[76] Inventor: Hiroshi Hukuba, No. 914-1, Nazukari, Nagareyama, Chiba, Japan

[21] Appl. No.: 215,678

[22] Filed: Mar. 22, 1994

Related U.S. Application Data

[63] Continuation of Ser. No. 870,896, Apr. 20, 1992, abandoned.

[30] Foreign Application Priority Data

| Apr. 22, 1991 | [JP] | Japan | 3-117967 |
| Aug. 30, 1991 | [JP] | Japan | 3-244757 |
| Oct. 19, 1991 | [JP] | Japan | 3-299703 |
| Jan. 16, 1992 | [JP] | Japan | 4-025807 |

[51] Int. Cl.⁶ .................. A61C 17/34; A46B 13/02
[52] U.S. Cl. .................. 15/22.1; 15/167.1; 15/172
[58] Field of Search ............ 15/22.1, 22.2, 167.1, 15/167.2, 172, 22.4

[56] References Cited

U.S. PATENT DOCUMENTS

| 1,327,807 | 1/1920 | Burleigh | 15/167.1 |
| 2,022,457 | 11/1935 | Brown | 15/22.4 |
| 4,149,291 | 4/1979 | Stoltz | 15/22.1 |
| 4,326,314 | 4/1982 | Moret et al. | 15/22.1 |
| 4,450,599 | 5/1984 | Scheller et al. | 15/22.1 |
| 4,458,374 | 7/1984 | Hukuba | 15/22.1 |
| 4,476,604 | 10/1984 | White et al. | 15/105 |
| 4,520,526 | 6/1985 | Peters | 15/167.1 |
| 4,726,806 | 2/1988 | Hukuba | 15/167.1 |
| 5,146,645 | 9/1992 | Dirksing | 15/167.1 |

FOREIGN PATENT DOCUMENTS

| 90309696 | 9/1990 | European Pat. Off. . | |
| 93309696 | 9/1990 | European Pat. Off. . | |
| 92303603 | 4/1993 | European Pat. Off. . | |
| 711331 | 9/1941 | Germany . | |
| 2756166 | 6/1979 | Germany . | |
| 485723 | 10/1953 | Italy | 15/143.1 |
| 4227372 | 8/1965 | Japan . | |
| 57-69806 | 4/1982 | Japan . | |
| 57-166108 | 10/1982 | Japan . | |
| 58-69505 | 4/1983 | Japan . | |
| 58-105709 | 6/1983 | Japan . | |
| 59-40807 | 3/1984 | Japan . | |
| 353122 | 5/1991 | Japan . | |
| 353123 | 5/1991 | Japan . | |
| 353124 | 5/1991 | Japan . | |

Primary Examiner—Edward L. Roberts, Jr.
Attorney, Agent, or Firm—Sixbey, Friedman, Leedom & Ferguson

[57] ABSTRACT

There is provided an electrically driven toothbrush having a simple structure and capable of changing the reciprocation stroke of bristles in a simple operation. The toothbrush is composed of a head portion 10 including a bristle portion 15 studded with bristles 14, a grip portion 12 having a motor 22, an intermediate transmission member 20 mounted in the grip portion and connected to the head portion, and a conversion mechanism 24 interposed between the intermediate transmission member and the motor for converting a rotational movement of the motor into a reciprocal movement of the intermediate transmission member. At least the bristle portion of the head portion is resiliently tiltable with respect to an axis of the intermediate transmission member, and at least the reciprocation stroke of the bristle portion can be changed in accordance with the tilting distance of the bristle portion.

12 Claims, 14 Drawing Sheets

F I G. 3
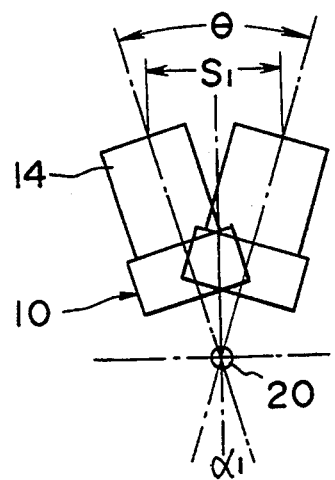
F I G. 4
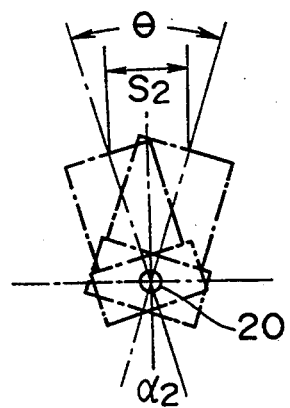
F I G. 5
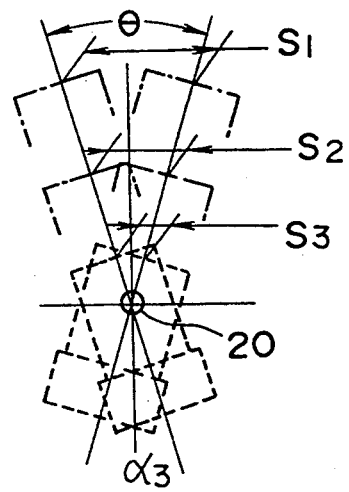

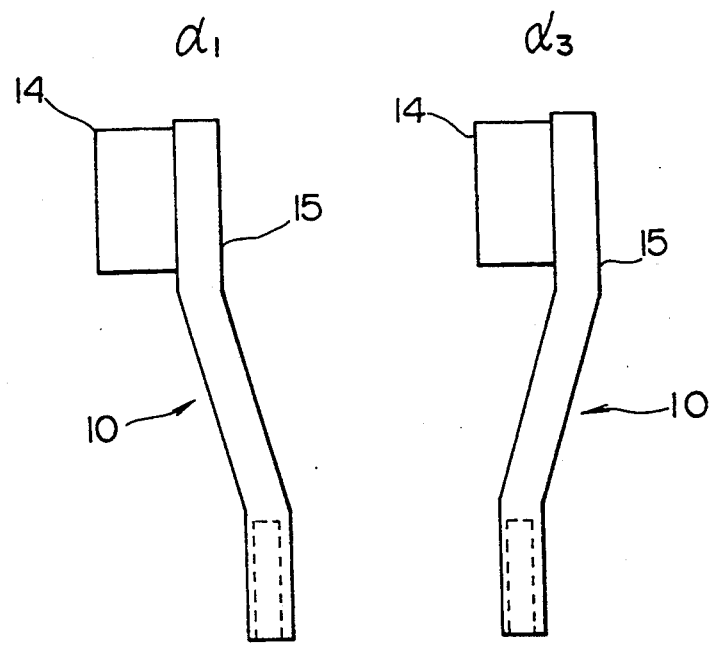

TOOTHBRUSH

This application is a Continuation of Ser. No. 07/870,896, filed Apr. 20, 1992, now abandoned.

BACKGROUND OF THE INVENTION

1. Field of the Invention

The present invention relates to a toothbrush.

2. Description of the Related Art

Various kinds of manners for cleaning teeth by a toothbrush have been suggested so far, and, above all, a so-called Bass or scrub method, in which bristles of a toothbrush are substantially reciprocated in the axial direction of the main body of the toothbrush at a short stroke of several millimeters, has been recently recognized to be the most effective in removing plaque. However, a pressure at which an ordinary person presses the bristles against teeth is approximately 300–500 g. In this case, the bristles of an ordinary toothbrush curl up at the ends, and it is difficult for the distal ends of the bristles to reach a portion between teeth or between teeth and gums where the plaque is apt to collect. Even if the ends of the bristles reach there, since they curl up, a satisfactory brushing effect cannot be obtained. As a result, it is not expected that the plaque will be removed by reciprocating the toothbrush at a short stroke. Furthermore, if the teeth are brushed under such a great pressure, the gums regress, and the surfaces of the teeth are worn out, this resulting into a wedge-shaped defect. Accordingly, the optimum pressure of the bristles is approximately 70–200 g. When the Bass or scrub method is carried out at this pressure, the ends of bristles reach a portion between the teeth and between the teeth and the gums where plaque causing pyorrhea, such as anaerobic bacteria, is most apt to collect. Since the plaque is stirred by the bristles, oxygen is supplied to the plaque, thereby controlling the increase of the plaque. In addition, a wedge-shaped defect and so on can be prevented.

Thus, in order to obtain a satisfactory brushing effect on teeth, while it is necessary to pay attention to the manner or direction of movement of the hand, it is very important to optimize the pressure of bristles of the toothbrush against teeth or the like. However, no well-known type of brush takes the brushing at the optimum pressure into consideration.

On the other hand, electrically driven toothbrushes each of which performs brushing by using an electric motor have been recently developed. Electrically driven toothbrushes disclosed in, for example, Japanese Patent Laid-Open Publication Nos. 57-166108, 58-69505 and 58-105709 and Japanese Patent Post-Examination Publication No. 42-27372 each substantially reciprocate the ends of bristles in the axial direction of a head portion at a short stroke of several millimeters. Furthermore, Japanese Patent Laid-Open Publication Nos. 59-40807 and 57-69806 disclose the reciprocal rotation of the ends of bristles around an axis of a head portion.

Such electrically driven toothbrushes are convenient to the user since he does not need to move his hand, while he becomes less attentive to brushing. In particular, the user is apt to be careless about the optimum pressure of bristles against teeth, and to inadvertently press the ends of the bristles of a reciprocating toothbrush against the teeth strongly, this causing damage to gums.

Furthermore, in the above conventional electrically driven toothbrushes, if bristles are pressed against the teeth with a relatively strong force in order to brush the teeth strongly, the load acting on a motor is increased, the rotation torque of the motor is decreased, and the reciprocation of the bristles is decelerated, and therefore, desired strong brushing cannot be achieved.

It is said that the stroke of the above linear or rotational reciprocation should be changed in accordance with a portion to be actually brushed. For example, in order to brush the surfaces of teeth or give a massage to gums, it is preferable that the reciprocation stroke be relatively large. To the contrary, when a narrow portion, for example, a portion between teeth, an occluding portion of teeth, or a boundary between teeth and gums, is brushed, the reciprocation stroke should be small. However, the above conventional electrically driven toothbrush cannot change the reciprocation stroke. Therefore, it is necessary to prepare a plurality of electrically driven toothbrushes having different reciprocation strokes in order to perform proper brushing depending on a portion to be brushed. Although it can be thought to use a motor serving as a drive source which can rotate in the normal and reverse directions, and to operate an electric switch so as to, for example, select a small reciprocation stroke in the normal rotation or a large reciprocation stroke in the reverse direction, the use of such an electric selection switch complicates the structure of the toothbrush, increases the cost, and causes trouble. Furthermore, it has been proposed that an intermediate transmission member for converting a rotational movement of a motor into a reciprocal movement and transmitting the reciprocal movement to a brush head is made to be tiltable from a reference position and the reciprocation stroke of the brush head is changed in accordance with the tilting distance of the intermediate transmission member (see, for example, U.S. Pat. No. 4,326,314). In this case, the structure of the toothbrush is complicated, the driving force transmission mechanism is apt to be broken down, and it is feared that a problem in sealing with respect to water will arise since the intermediate transmission member itself tilts.

SUMMARY OF THE INVENTION

With the above problems of the prior art in view, an object of the present invention is to provide a toothbrush capable of obtaining the optimum pressure of the toothbrush against teeth without the user's skill and close attention.

Another object of the present invention is to provide an electrically driven toothbrush having a buffer function with respect to teeth and so on when pressing bristles against the teeth.

A further object of the present invention is to provide an electrically driven toothbrush having a simple structure, and capable of changing the reciprocation stroke of bristles in a simple operation and efficiently performing satisfactory brushing.

In order to achieve the above objects, according to one aspect of the present invention, there is provided a toothbrush comprising a bristle portion studded with bristles and a grip portion adapted to be gripped by the user, wherein at least the bristle portion is resiliently and tiltably supported by the grip portion so as to tilt in response to a pressure against teeth.

According to the above construction, even if bristles are strongly pressed against teeth, the bristles resiliently tilt. Within a predetermined range where the bristles can tilt, an urging force supplied from the user's hand does not directly correspond to a pressure of the bristles and it is reduced. Since a pressure supplied through a conventional toothbrush by an ordinary person is larger than the optimum pressure as described above, as long as the user does not press the toothbrush with an extremely large force, the pressure against the teeth accords with or approximates the optimum reduced pressure. It is thereby possible to prevent regression of gums and wear of teeth and to effectively remove plaque.

According to another aspect of the present invention, there is provided a toothbrush comprising a head portion including a bristle portion studded with bristles, a grip portion having a motor, an intermediate transmission member or a coupling member reciprocally supported by the grip portion and connected to the head portion, and a conversion mechanism interposed between the intermediate transmission member and the motor for converting a rotational movement of the motor into a reciprocal movement of the intermediate transmission member, wherein at least the bristle portion of the head portion is tiltable from a reference position. The bristle portion may be substantially urged in a direction toward distal ends of the bristles and resiliently tiltable in response to pressing the bristles against teeth. According to this construction, even if the bristles are inadvertently pressed against the teeth too strongly, the bristles resiliently tilt and retreat, thereby preventing the teeth from being damaged.

The bristle portion can be displaced from the axis of the intermediate transmission member by the above tilting movement, and the stroke of reciprocation of the bristle portion can vary depending on the displaced distance.

When at least the bristle portion of the head portion is tilted from the axis of the intermediate transmission member, the reciprocal movement of the tilted bristle portion differs from that of the intermediate transmission member, and the reciprocation stroke of the bristle portion varies depending on the tilting distance. Therefore, it is unnecessary to employ a complicated structure to change the reciprocation stroke by, for example, operating an electric switch or tilting the intermediate transmission member with respect to a conversion mechanism. The tilting of the bristle portion from the axis of the intermediate transmission member may be performed by adjusting the pressure of the bristles against teeth in brushing, manually moving the bristle portion beforehand, or preparing a plurality of head portions having different tilted angles and connecting one of the head portions to the intermediate transmission member in accordance with a desired reciprocation stroke. If the tilted angle is changed by the adjustment of the pressure of the bristles against the teeth in brushing, the load acting on the motor is substantially constant within at least a range where the bristle portion can tilt, and the rotational speed of the motor is not decreased as long as the bristles are pressed in the range. If the reciprocation stroke is set small when the pressure is high and large when the pressure is low, a work of the bristles is substantially constant and efficient brushing can be achieved.

BRIEF DESCRIPTION OF THE DRAWINGS

FIG. 3 is a schematic view of the embodiment showing the reciprocal movement when a bristle portion is in a state $\alpha_1$;

FIG. 4 is a schematic view of the embodiment showing the reciprocal movement when the bristle portion is in a state $\alpha_2$;

FIG. 5 is a schematic view of the embodiment showing the reciprocal movement when the bristle portion is in a state $\alpha_3$;

FIGS. 16(A) and (B) are side views of a head portion in states $\alpha_1$ and $\alpha_3$, respectively, according to a seventh embodiment of the present invention;

DESCRIPTION OF THE PREFERRED EMBODIMENTS

Preferred embodiments of the present invention will now be described with reference to the accompanying drawings.

Figure 1:
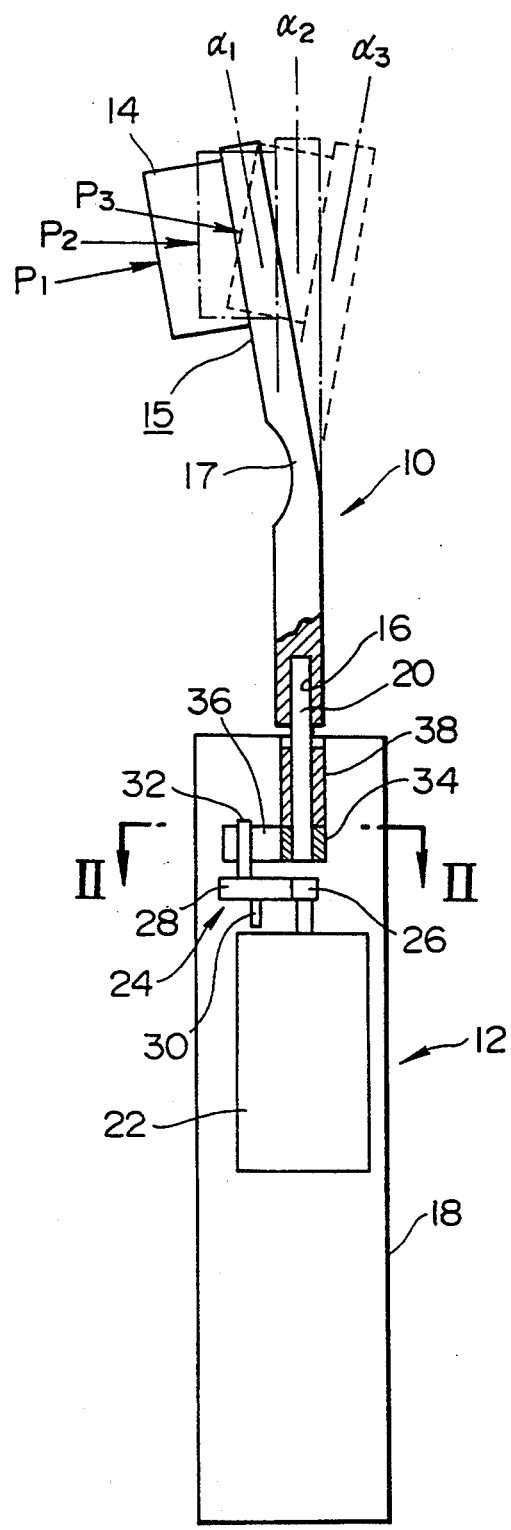
FIG. 1 is a schematic view of an electrically driven toothbrush according to a first embodiment of the present invention.
Figure 2:
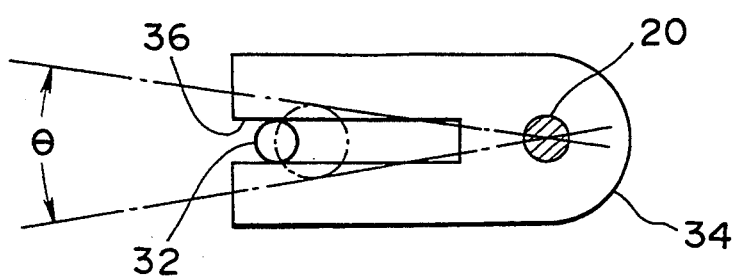
FIG. 2 is an enlarged sectional view taken along line II—II of FIG. 1.

FIGS. 1 and 2 each illustrate a first embodiment of the present invention. An electrically driven toothbrush mainly consists of a head portion 10 and a grip portion 12. The head portion 10, detachable from the grip portion 12, is formed with a bristle portion 15 studded with bristles 14 at the head thereof and a support shaft insertion hole 16 at the bottom thereof, and detachably connected to a support shaft 20, described below, through the support shaft insertion hole 16. The head portion 10 is made of synthetic resin or the like having flexibility and resilience, and formed with a bending portion 17 whose center portion is partially cut off. The head portion 10 is bent toward distal ends of the bristles 14 at the bending portion 17 beforehand in a normal state, that is, when no force or a relatively small force $P_1$ acts on the surface of the bristles 14. As the leading end of the bristle portion 15 is approached, the amount of displacement of the bristle portion from the axis of the support shaft 20 gradually increases (a state $\alpha_1$). If greater forces $P_2$ and $P_3$ act on the surface of the bristles 14, the head portion 10 is resiliently raised up and put into states $\alpha_2$ and $\alpha_3$.

The grip portion 12 has the support shaft 20 projecting from an outer casing 18 in a direction of the leading end of the grip portion 12, and the head portion 10 is detachably attached to the grip portion 12 by fitting the support shaft 20 in the support shaft insertion hole 16 of the head portion 10. The grip portion 12 is mainly composed of a motor 22 accommodated in the outer casing 18, a conversion mechanism 24 for converting the rotation of the motor 22 into the reciprocal rotation, and the aforementioned support shaft 20 for receiving the reciprocal rotation from the conversion mechanism 24. The rotational force of the motor 22 is first transmitted from a pinion 26 to an intermediate gear 28 which is rotatably supported by a shaft 30 substantially supported by the outer casing 18. An eccentric projection 32 which is eccentric to the shaft 30 projects from the leading face of the intermediate gear 28. The eccentric projection 32 is, as shown in FIG. 2, engaged with an elongated hole 36 of a tilting member 34 formed like an almost U-shaped slot as a whole, and the tilting member 34 is integrally mated with the bottom of the aforementioned support shaft 20 and extended in the radial direction of the support shaft 20. Therefore, the eccentric projection 32 eccentrically rotates while sliding in the elongated slot 36 of the tilting member 34 in correlation to the rotation of the intermediate gear 28 on the shaft 30, thereby performing the reciprocal rotation of the tilting member 34 and the support shaft 20 at a predetermined rotation angle. Almost the center of the support shaft 20 is rotatably supported by a support member 38 fixed inside the outer casing 18 and held in a fixed reference position.

According to the above mechanism, the rotational force of the motor 22 is transmitted to the intermediate gear 28 through the pinion 26. In correlation to the rotation of the intermediate gear 28 on the shaft 30, the eccentric projection 32 eccentrically rotates while drawing an arc shown in FIG. 2, thereby causing the tilting movement, that is, the reciprocal rotation of the tilting member 34 and the support shaft 20 on the axis of the support shaft 20.

FIGS. 3 to 5 are top views of the head portion 10 shown in FIG. 1. FIG. 3 shows that the bristle portion 15 of the head portion 10 is in the state $\alpha_1$ under the pressure $P_1$, FIG. 4 shows that the bristle portion 15 is in the state $\alpha_2$ under the pressure $P_2$, and FIG. 5 shows that the bristle portion 15 is in the state $\alpha_3$ under the pressure $P_3$. As shown in these figures, even if the reciprocal rotation of the support shaft 20 is performed at an angle $\theta$, if the distal ends of the bristles 14 are the farthest from the shaft 20 as shown in FIG. 3, a reciprocation stroke of the bristles 14 is the longest $S_1$, and the stroke becomes an intermediate value $S_2$ in the state of FIG. 4. As shown in FIG. 5, when the distal ends of the bristles 14 are the nearest to the shaft 20, the reciprocation stroke of the bristles 14 is the shortest $S_3$. As described above, in this embodiment, it is possible to change the reciprocation stroke of the ends of the bristles 14 by changing the pressure to the bristles 14, that is, the pressure of the bristles 14 against teeth in brushing without changing the structure of the conversion mechanism 24 for converting the above rotational force into the reciprocal rotation force.

For example, in order to brush the surfaces of teeth or massage gums, it is only necessary to put at least the bristle portion 15 into the state $\alpha_1$ without pressing the bristles 14 against the teeth so strongly. The bristles 14 thereby perform the reciprocal rotation at a large reciprocation stroke so as to efficiently and satisfactorily execute brushing and the massage. On the other hand, in order to brush an uneven portion, such as a portion between teeth and a boundary portion between teeth and gums, the bristles 14 are strongly pressed against the teeth and the bristle portion 15 is put into the state $\alpha_3$. The distal ends of the bristles 14 thereby reciprocate at the short stroke $S_3$, brushing similar to the so-called Bass or scrub method can be achieved, and plaque can be efficiently removed. Within a range where the bristle portion 15 resiliently tilts, even if the distal ends of the bristles 14 are pressed against teeth strongly, a great load does not act on the motor 22, and the rotational speed of the motor 22 is not reduced unlike before. In particular, since the reciprocation stroke is large when the pressure P is small and small when the pressure P is large, a work of the bristles 14 is substantially constant regardless of the tilting position of the bristle portion 15.

Thus, since the reciprocation stroke of the distal ends of the bristles is changed merely by changing the pressure of the bristles against teeth without, for example, operating a switch or displacing the support shaft 20 in a conventional manner, the structure of the toothbrush is simplified, the number of breakdowns is reduced, and sealability with respect to water is improved in comparison with the case in which the support shaft 20 is displaced. Furthermore, since at least the bristle portion 15 of the head portion 10 can resiliently tilt, even if the bristles 14 are inadvertently pressed against the teeth strongly, the bristles 14 resiliently retreat, that is, have a buffer function with respect to the teeth. This advantage is remarkable particularly when the bristles 14 of the driving head portion 10 are first brought into contact with the teeth. Then, since the bristle portion 15 is urged to be pressed against the teeth, the bristles 14 can automatically trace the uneven portions of the teeth when the whole toothbrush is moved. In particular, brushing of the complicated uneven portions can be effectively performed without any special attention of the user.

It should be understood that this embodiment includes a grip portion 12 replaced with a grip of an ordinary toothbrush, and a proper pressure can also be secured in this case.

Figure 6:
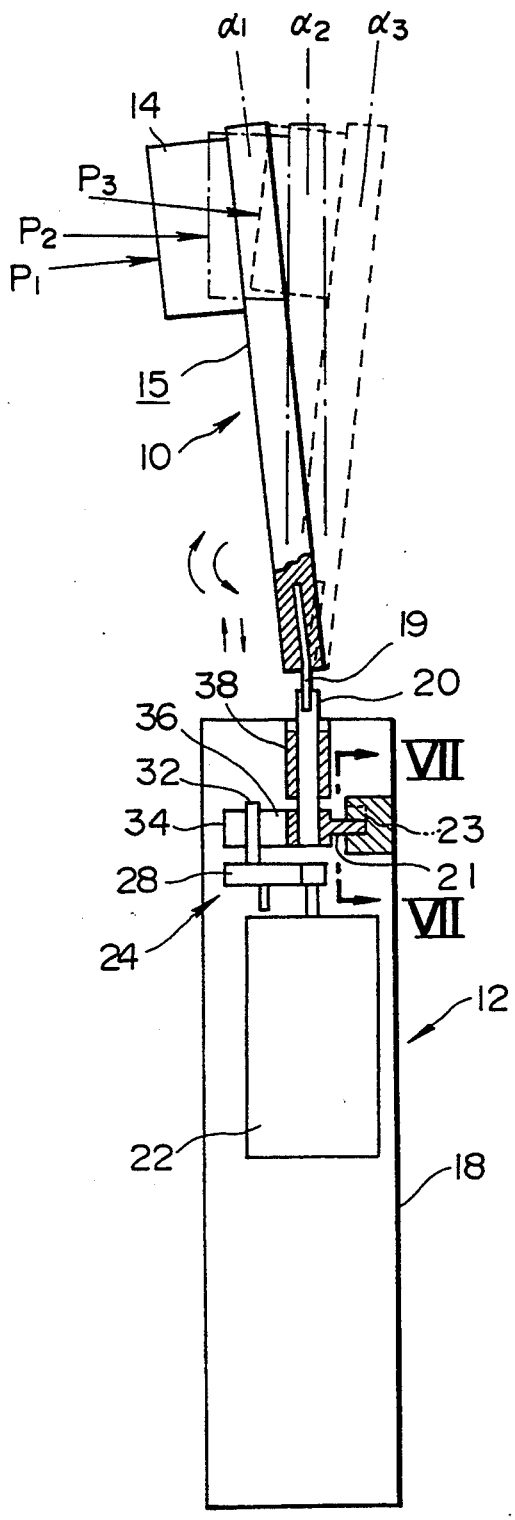
FIG. 6 is a schematic view of a second embodiment of the present invention.
Figure 7:
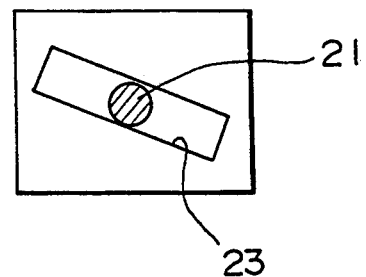
FIG. 7 is an enlarged sectional view taken along line VII—VII of FIG. 6.

FIG. 6 illustrates a second embodiment of the present invention. This embodiment is different from the first embodiment shown in FIG. 1 in that a resilient strip 19 projecting toward the bottom of a head portion 10 is attached to the bottom of the head portion 10, connected to a support shaft 20 and made resiliently tiltable instead of positively bending the body of the head portion 10. In particular, the resilient strip 19 is bent beforehand in this embodiment and the head portion 10 is put into a position $\alpha_1$ indicated by a solid line when a pressure $P_1$ acts on bristles 14. Furthermore, the support shaft 20 performs not only reciprocal rotation on the shaft thereof, but also reciprocation in the axial direction thereof. In other words, a guide pin 21 projecting in a direction reverse to an elongated slot 36 of a tilting member 34 is integrally formed at the bottom of the tilting member 34, and inserted so as to slide along a guide slot 23 integrally formed inside an outer casing 18. The guide slot 23 extends with an inclination with respect to the direction perpendicular to the axis line of the support shaft 20 as shown in FIG. 7. Therefore, although the pin 21 also moves in correlation to the above tilting movement of the tilting member 34, since the guide slot 23 is inclined, the tilting member 34 also reciprocates in the axial direction of the support shaft 20.

According to the construction of the second embodiment, the support shaft 20 is held in a fixed position with respect to a conversion mechanism 24. The head portion 10 is slightly raised up while resiliently transforming the resilient strip 19 and put into the state $\alpha_2$ when a pressure $P_2$ greater than $P_1$ acts on the bristles 14. When an even greater pressure $P_3$ acts on the bristles 14, the head portion 10 is put into the state $\alpha_3$. Therefore, the radial distance of the distal ends of the bristles 14 with respect to the support shaft 20 is changed as shown in FIGS. 3 to 5 in the same manner as in the first embodiment, thereby changing the reciprocation stroke of the bristles 14.

It should be understood that this embodiment also includes a grip portion 12 replaced with a grip of an ordinary toothbrush.

Figure 8:
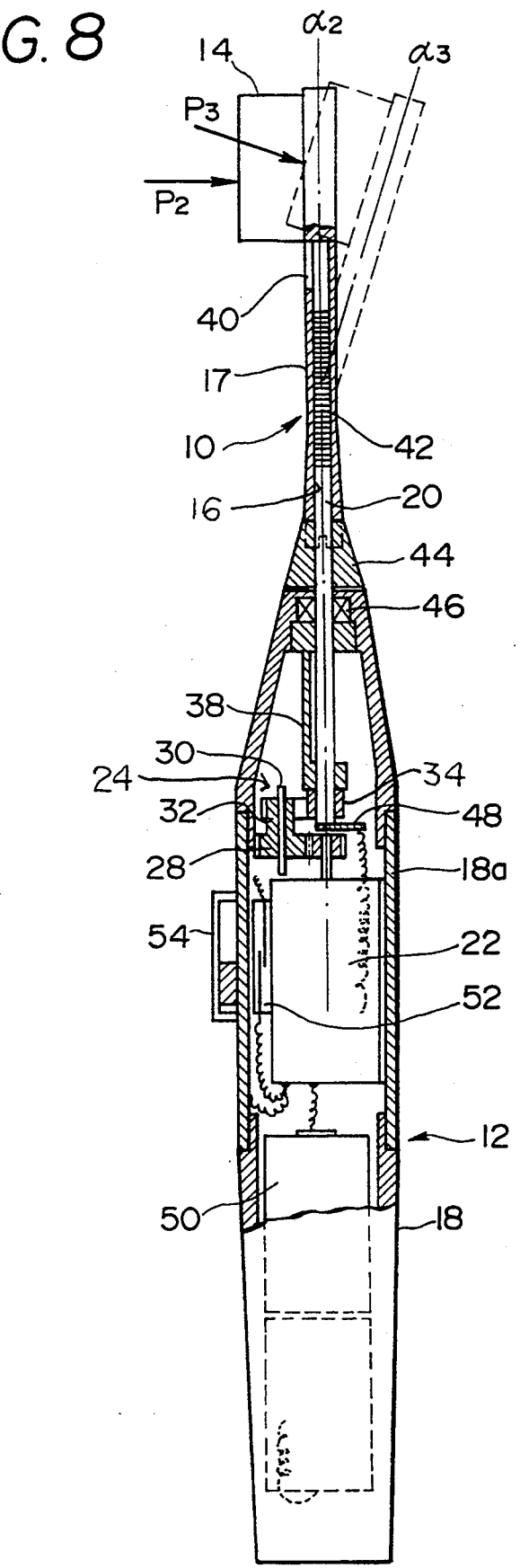
FIG. 8 is a broken sectional view of the principal part according to a third embodiment of the present invention.

FIG. 8 illustrates a third embodiment of the present invention. The third embodiment differs from the first embodiment in using a so-called electronic toothbrush for producing the flow of electrons between teeth and bristles through the human body. In other words, a head portion 10 has a support shaft insertion hole 16 extending from the bottom of the head portion 10 to the adjacency of the bottom of bristles 14 in the axial direction. The bottom of the support shaft insertion hole 16 and thus the end of the support shaft is exposed to the bristled side of the head portion 10 through a connecting hole 40 near the bristles 14. The connecting hole 40 functions as a part of a liquid path for forming a conductive path by using liquid as a medium in order to electrically connect a support shaft 20 inserted in the support shaft insertion hole 16 and the bristles 14 through the liquid, for example, saliva. Almost the center of the head portion 10 away from a bristle portion 15 is formed as a bending portion 17 whose thickness to the support shaft insertion hole 16 is relatively small. Therefore, the head portion 10 itself tilts at the bending portion 17 as a fulcrum in the same manner as in the first embodiment.

The support shaft 20, made of a conductive material and projecting from a grip portion 12, extends so as to reach the innermost portion of the support shaft insertion hole 16, and a portion thereof corresponding to the bending portion 17 of the head portion 10 is formed of a coil spring 42. Alternatively, the support shaft 20 can be entirely made of a coil spring or formed into any shape, as desired. Therefore, the support shaft 20 can bend together with the head portion 10. Reference numeral 44 denotes a retaining member on the side of the grip portion 12 which is mated with the support shaft 20 and detachable from a retaining mechanism at the bottom of the head portion 10. Reference numeral 46 denotes a sealing portion. Furthermore, an eccentric projection 32 of an intermediate gear 28 has a relatively long diameter and a rotation center shaft 30 penetrates forward and backward in a position shifted from the center of the eccentric projection 32.

An end of the support shaft 20 projecting from a tilting member 34 is in contact with a conductive plate 48 which is connected to one of poles of a battery 50 accommodated in an outer casing 18, for example, a negative pole. The outer casing 18 is divided into three members in the axial direction, and the center member is a conductive cylinder 18a plated with conductive metal on both sides so as to have conductivity. The other pole of the battery 50, for example, a positive pole is connected to the rear side of the conductive cylinder 18a through a lead switch 52. Reference numeral 54 denotes a switch knob.

Figure 9:
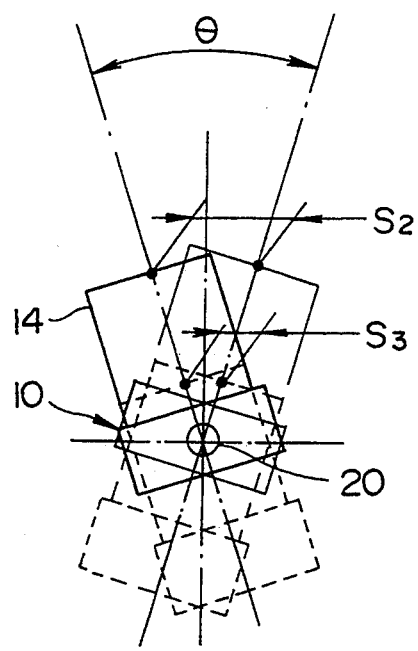
FIG. 9 is a schematic view of the same position as FIG. 3 showing the reciprocal movement of the third embodiment.
Figure 10:
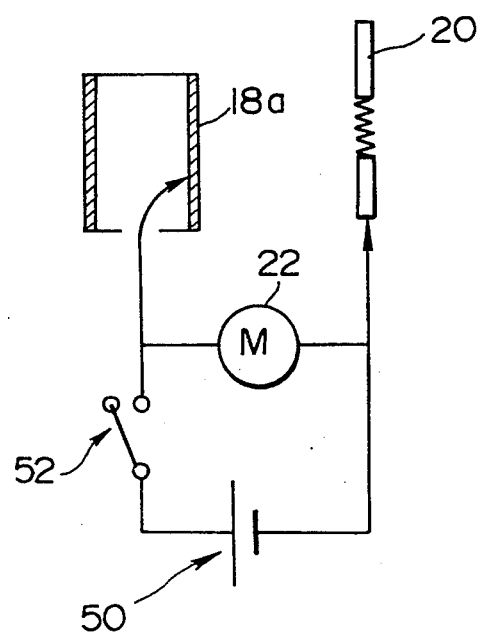
FIG. 10 is a circuit diagram showing an electric circuit of the third embodiment.

Referring to FIG. 10, when the lead switch 52 is actuated by operating the switch knob 54, a motor 22 is rotated, and the head portion 10 thereby performs reciprocal rotation on the support shaft 20 through a conversion mechanism 24 and the support shaft 20. If the user grips the grip portion 12 by hand, particularly touches the conductive cylinder 18a, inserts the bristles 14 into the mouth and performs brushing, the bristles 14 and the connecting hole 40 of the head portion 10 are made wet with saliva and so on. This forms an electric circuit linking the battery 50, the conductive cylinder 18a, the hand, the body, the teeth, the bristles 14, liquid like saliva, the support shaft 20 and the battery 50 in this order, thereby generating a flow of electrons and effectively removing plaque from the surfaces of teeth. In a state $\alpha_2$ of the head portion 10 indicated by a solid line in FIG. 8, a pressure $P_2$ acts on the bristles 14. If a pressure $P_3$ greater than $P_2$ is applied, the bending portion 17 of the head portion 10 is resiliently transformed with the coil spring 42 of the support shaft 20, and put into a state $\alpha_3$. Thereby, as shown in FIG. 9, since a reciprocation stroke $S_2$ in the state $\alpha_2$ is changed to a smaller stroke $S_3$ in the state $\alpha_3$ since the distal ends of the bristles 14 approach the support shaft 20 in the radial direction.

It should be understood that this embodiment also includes a grip portion 12 replaced with a grip of an ordinary toothbrush or an ordinary electronic toothbrush having no conversion mechanism.

Although not shown in the drawings, the connecting hole in this embodiment can be replaced by an electrically conductive member, or the bristles can be physically connected with the support shaft 20 through an electrically conductive member extending from the bristles to the support shaft 20. Furthermore, a part of the support shaft 20, especially the portion projecting from the retaining member 44 can alternatively be fixed in the head portion 10, while the remaining portion of the support shaft 20 terminates at the retaining member 44.

Figure 11:
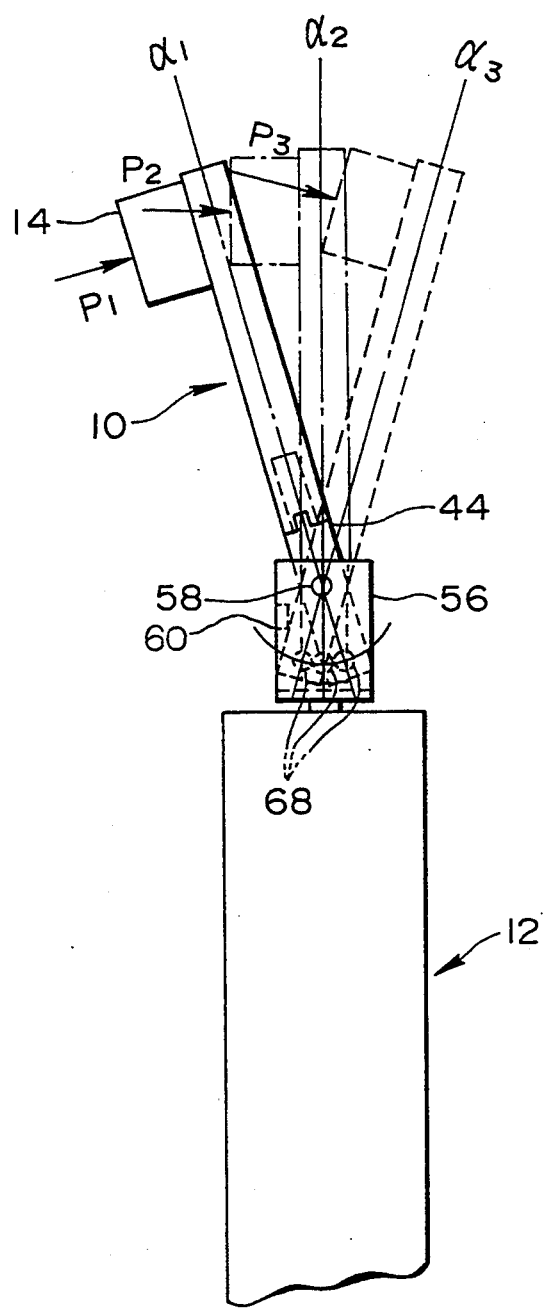
FIG. 11 is a side view of the principal part according to a fourth embodiment of the present invention.
Figure 12:
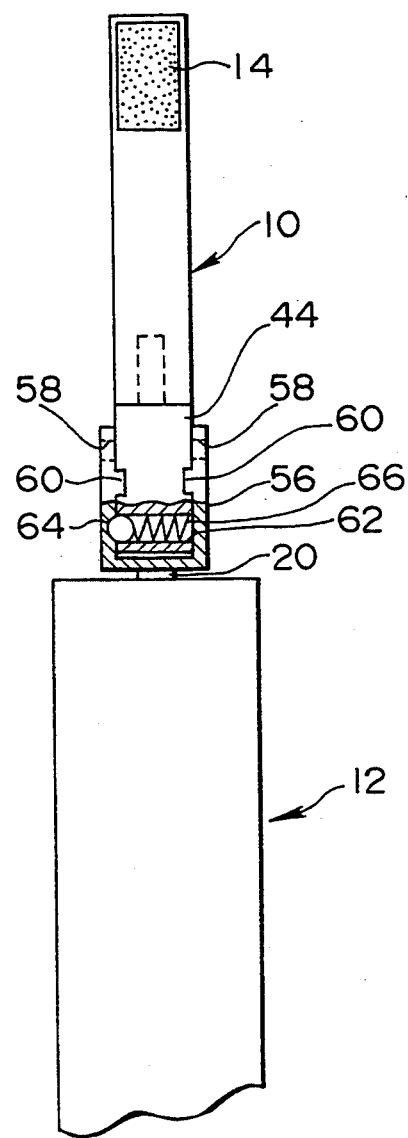
FIG. 12 is a front view taken from the left side of FIG. 11.

FIGS. 11 and 12 each illustrate a fourth embodiment of the present invention. While the bristle portion 15 of the head portion 10 analogously tilts depending upon the pressure of the bristle portion 15 against teeth in the above first to third embodiments, moderate digital tilting of a bristle portion 15 is carried out in the fourth embodiment. In other words, an end of a support shaft 20 projecting a grip portion 12 is connected to a substantially U-shaped receptacle 56, from which a retaining member 44 to be engaged with the bottom of a head portion 10 projects. The retaining member 44 is tiltably supported in the receptacle 56 through a pin 58, and the tilting range of the retaining member 44 is regulated by a stopper 60 projecting inside the receptacle 56. The bottom of the retaining member 44 is formed with a hole 62 which penetrates in the direction of the width of the retaining member 44. A ball 64 is retractably mounted in the hole 62, and urged by a coil spring 66 so as to project from the retaining member 44 toward the inner wall of the receptacle 56. On the other hand, the inner wall of the receptacle 56 opposite to the ball 64 is formed with a plurality of, for example, three concave portions 68 to receive the ball 64.

According to the above construction, when the head portion 10 is in a position $\alpha_1$, $\alpha_2$ or $\alpha_3$, the ball 64 in the retaining portion 44 can be fitted and positioned in one of the concave portions 68. In this embodiment, although the head portion 10 can be held in the position $\alpha_1$, $\alpha_2$ or $\alpha_3$ in accordance with the pressure of the heading portion 10 against teeth in brushing, brushing can be also performed in a state where the head portion 10 is manually put into a desired position beforehand. Furthermore, in this embodiment, the reciprocation stroke of the bristles 14 can be decreased as the pressure against the teeth increases in the same manner as the above embodiments by urging the retaining member 44 in the direction of $\alpha_1$ by a spring or the like. If the bristles 14 come loose, it is necessary to separate the head portion 10 from the retaining member 44 and replace the head portion 10 with a new one.

It should be understood that: this embodiment also includes a grip portion 12 replaced with a grip of an ordinary toothbrush.

Figure 13:
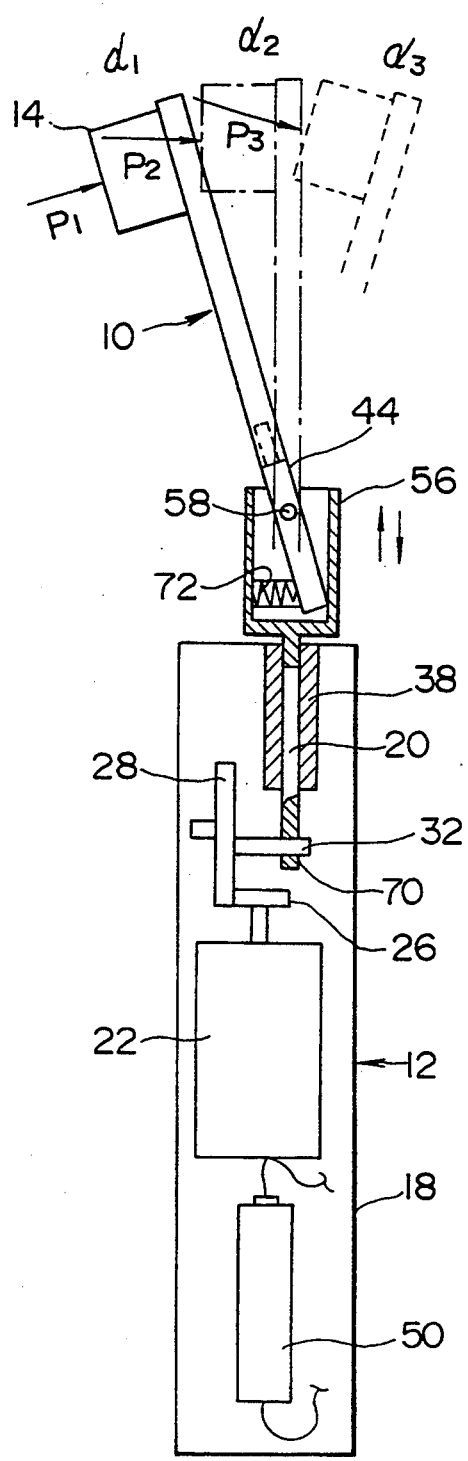
FIG. 13 is a schematic view of a fifth embodiment of the present invention.
Figure 14:
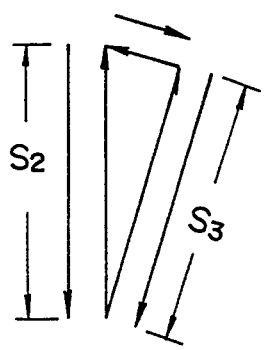
FIG. 14 is an explanatory view showing the reciprocal movement of the fifth embodiment.

A fifth embodiment of the present invention is illustrated in FIGS. 13 and 14. The fifth embodiment is different from the above embodiments in the following points. First, an intermediate gear 28 is a bevel gear and its rotational axis is perpendicular to an axis of a pinion 26 of a motor 22. An eccentric projection 32 of the intermediate gear 28 is inserted in a hole 70 formed at the bottom of a support shaft 20 which is slidable with respect to a support member 38 in the axial direction. An end of the support shaft 20 projecting from a grip portion 12 is connected to a receptacle 56 in the same manner as the aforementioned fourth embodiment, and the receptacle 56 tiltably supports a retaining member 44 on a pin 58, and is detachably connected to a head portion 10. The bottom of the retaining member 44 is urged by a coil spring 70 so that the head portion 10 is in a state $\alpha_1$.

According to the above construction, if the hole 70 is elongated in a direction perpendicular to a paper plane of FIG. 13, the support shaft 20 reciprocates in the axial direction. If the hole 70 is a round hole having almost the same diameter as that of the eccentric projection 32, a portion of the hole 70 makes circular motion in correlation to the movement of the eccentric projection 32, and, for example, if the support shaft 20 is tiltably supported near the leading end of the support member 38, not only the receptacle 56 but the bristles 14 similarly makes circular or elliptic motion. In other words, the reciprocal movement of the support shaft 20 is performed on a plane perpendicular to a paper plane of FIG. 13 including the axis of the support shaft 20.

According to this embodiment, when the head portion 10 is positioned concentrically with the support shaft 20 in a state $\alpha_2$, the reciprocation stoke of the bristles 14 is the same as that of the support shaft 20. Referring to FIG. 14, when the head portion 10 is in a state $\alpha_3$, a reciprocation stroke $S_3$ of the head portion 10 in the axial direction is shorter than $S_2$ in the state $\alpha_2$, and the head portion 10 also starts reciprocation in the extending direction of the bristles 14. This is the same as in the case where the head portion 10 is in a state $\alpha_1$. In this embodiment, the support shaft 20 serving as a coupling member is held in a fixed position with respect to the eccentric projection 32 of the conversion mechanism in the extending direction of the bristles 14.

It should be understood that this embodiment also includes a grip portion 12 replaced with a grip of an ordinary toothbrush.

Figure 15A:
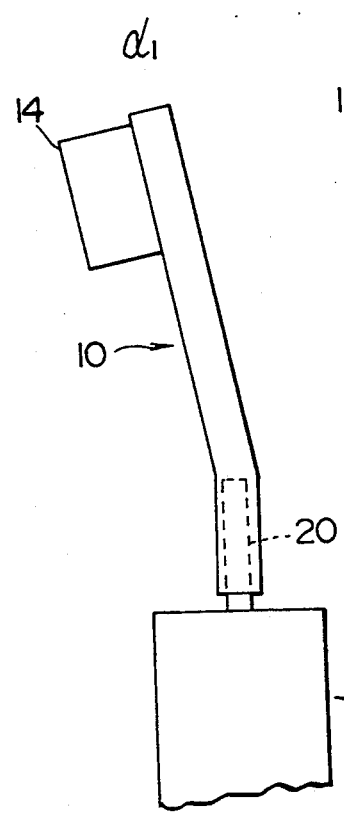
FIGS. 15(A), (B) and (C) are side views of a head portion in states $\alpha_1$, $\alpha_2$ and $\alpha_3$, respectively, according to a sixth embodiment of the present invention.
Figure 15B:
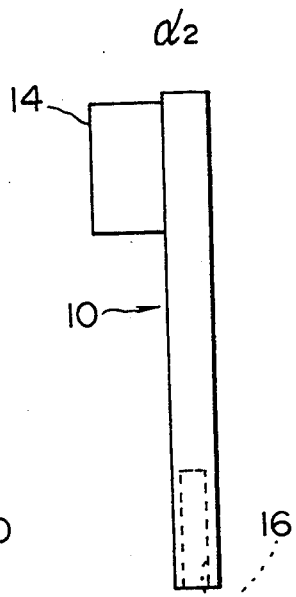
Figure 15C:
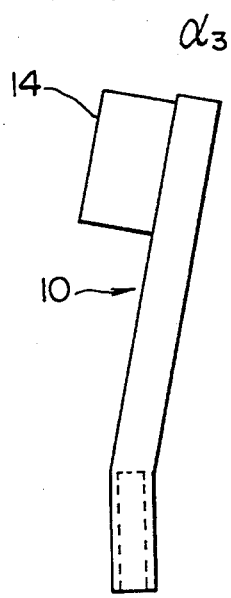

FIG. 15 shows a sixth embodiment of the present invention. While one head portion 10 itself tilts in the first embodiment, the sixth embodiment prepares a plurality of head portions 10 shaped in states $\alpha_1$ to $\alpha_3$, selects one of the head portions 10 in accordance with a desired reciprocation stroke, and attaches the selected head portion 10 to a support shaft 20. In this embodiment, even if the pressure of bristles 14 against teeth varies, the reciprocation stroke of the bristles 14 does not change.

A seventh embodiment of the present invention is illustrated in FIG. 16. Although this embodiment prepares a plurality of head portions 10 in various shapes in the same manner as the sixth embodiment, the bending shapes of the head portions 10 are different from those of the sixth embodiment. In other words, for example, two head portions 10 in states $\alpha_1$ and $\alpha_3$ each are substantially bent like a crank so that a bristle portion 15 is parallel to a support shaft 20.

Figure 17:
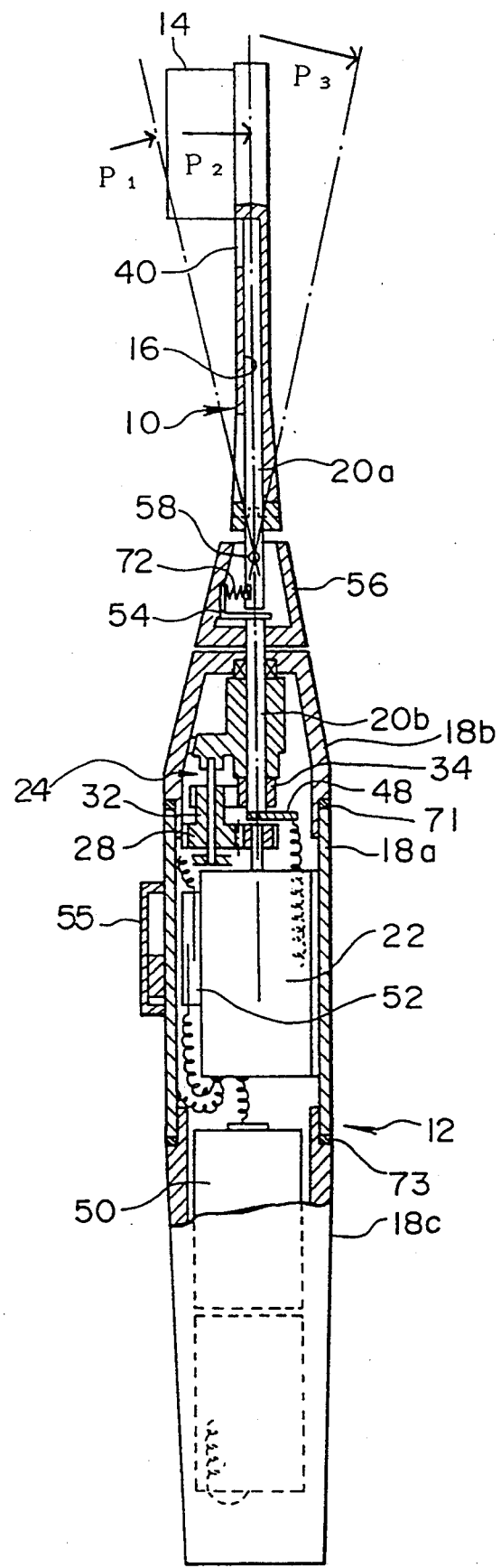
FIG. 17 is a broken sectional view showing the principal part according to an eighth embodiment of the present invention.
Figure 18:
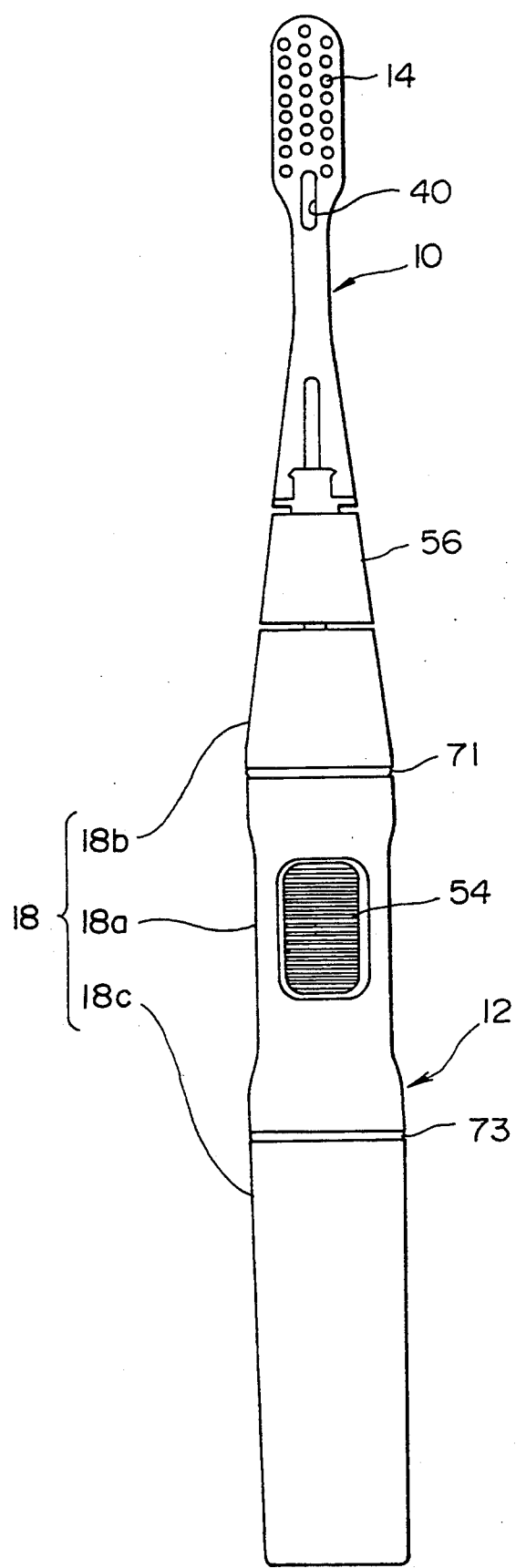
FIG. 18 is a front view of the eighth embodiment.

FIGS. 17 and 18 each show an eighth embodiment of the present invention. This embodiment is substantially a combination of the third embodiment shown in FIG. 8 and the fifth embodiment shown in FIG. 13. In other words, an electrically conductive support shaft ms divided in two, and one of the divided shafts 20b on the bottom side is reciprocally rotated around the axis by a conversion mechanism. The support shaft 20b is connected to one pole of a battery 50 at the bottom thereof through a conductive plate 48, and the leading end of the support shaft 20b is projected from a grip portion 12, and integrally fixed to a receptacle 56 in contact with a L-shaped connecting fitting 54 in the receptacle 56. The other support shaft 20a on the leading side, which can be in a different shape from the support shaft 20b and is in contact with the connecting fitting 54 at the end thereof through a coil spring 72, is tiltably supported with respect to the receptacle 56 through a pin 58, and held in contact with the connecting fitting 54 while being tilted. FIG. 17 illustrates the case in which a head portion 10 is in a position $\alpha_2$. The support shaft 20a is urged toward the distal ends of bristles 14 by the spring 72, and the head portion 10 is in a position $\alpha_1$ when the toothbrush is not being used or when the minimum pressure $P_1$ acts on the bristles 14. With the increase of the pressure to $P_2$ and $P_3$, the head portion 10 tilts to positions $\alpha_2$ and $\alpha_3$. The same reference numerals as those in FIG. 8 denote like components, and the description of the components is omitted. This embodiment provides an electrically driven toothbrush whose bristles reciprocate and rotate.

An outer casing 18 is, as shown in FIG. 18, divided into three cylindrical members (18b, 18a, 18c) in the lengthwise direction. The divided cylindrical members 18b, 18a and 18c are connected to one another through O-rings 71 and 73 for sealing, thereby constituting a housing for accommodating a motor and so on therein. The first cylindrical member 18b at the leading end of the outer casing 18 has a small diameter and is shaped like a truncated cone which broadens at the bottom, and the third cylindrical member 18c at the bottom is in the shape of a truncated cone which broadens at the leading end. The second cylindrical member 18a in the center is formed with a switch knob 54 on the outer wall, and the center portion of the second cylindrical member 18a has a little smaller diameter than those of both ends in the lengthwise direction for the purpose of easy gripping since the second cylindrical member 18a is most frequently gripped by the user.

Since the outer casing 18 of the grip portion 12 is thus divided into three, the degree of freedom for molding the outer casing 18 is enhanced so that the second cylindrical member 18a in the center can have a smaller diameter than other cylindrical members. In other words, since the second cylindrical member 18a is a cylinder which is open at both ends, it is possible in molding to draw molds out from both ends in the lengthwise direction and thus to form such a substantially bobbin-like cylinder. This is impossible if the outer casing 18 is integrally formed or divided in two.

In this embodiment, since the toothbrush functions as an electrically driven toothbrush as described above, the front and rear faces of the second cylindrical member 18a is plated with metal, and one pole of the battery 50 is connected to the rear face.

As described above, since the outer casing 18 of the grip portion 12 is divided into three cylindrical members, the second cylindrical member 18a which is most frequently gripped by the user can have the minimum diameter, thereby greatly improving operability of the toothbrush and providing the grip portion 12 which looks neat on the outside.

It is needless to say that the grip portion 12 may be divided into more than four parts, instead of three in the present invention. Furthermore, the present invention may be applied to not only an electrically driven toothbrush, but also a toothbrush accommodating other mechanisms and an actuator in a grip portion.

As described above, according to this embodiment, since the grip portion is divided into at least three cylindrical members in the lengthwise direction, it is possible to mold the divided cylindrical members independently, to increase the degree of freedom in the direction to draw molds out in molding, and to determine the shapes of the cylindrical members more freely. As a result, there can be provided a grip portion which has high operability and looks fine on the outside.

Furthermore, it should be understood that this embodiment also includes a grip portion 12 replaced with a grip of an ordinary toothbrush or an ordinary electronic toothbrush having no conversion mechanism.

What is claimed is:

1. A toothbrush, comprising:
   a head portion including a bristle portion studded with bristles;
   a grip portion adapted to be gripped manually and being a separate member from said head portion;
   a receptacle outside of and connected to a distal end of said grip portion;
   a connecting member pivotally supported within said receptacle and adapted to be coupled with said head portion such that said head portion, when connected with said connecting member, is pivotally connected to the grip portion; and
   resilient means disposed within said receptacle and engaged against said connecting member for urging said connecting member in a direction such that said bristle portion of said pivotally connected head portion is urged toward teeth of a user.

2. A toothbrush according to claim 1, further comprising:
   a battery accommodated in said grip portion;
   a grip conductor member covering a surface of said grip portion and connected with one pole of said battery;
   a second electrical conductor member on said grip portion connected with the other pole of said battery; and
   means for electrically connecting said bristles with said second electrical conductor member.

3. A toothbrush, comprising:
   a head portion including a bristle portion studded with bristles;
   a grip portion adapted to be gripped manually and being a separate member from said head portion;
   coupling means for detachably coupling said head portion to said grip portion and including means for providing said head portion with a tilting motion relative to said grip portion, in response to pressure applied to said bristle portion including
   a receptacle at a distal end of said grip portion;
   a connecting member having one end pivotally supported within said receptacle and other end adapted to be coupled with said head portion; and
   spring means disposed within said receptacle for urging said connecting member in a tilting direction toward distal ends of said bristles with respect to said head portion coupled with said other end of said connecting member.

4. An electrically driven toothbrush comprising:
   a head portion including a bristle portion studded with bristles, wherein at least said bristle portion in said head portion is tiltable from a reference position;
   a grip portion adapted to be gripped manually and accommodating an electric motor and being a separate member from said head portion;
   coupling means for coupling said head portion to said grip portion, said coupling means supported on said grip portion in such a manner that said coupling means makes a reciprocal movement and having a pivotal connecting member for pivotally connecting said head portion to said grip portion for providing said head portion with a tilting motion relative to the grip portion in response to pressure applied to said bristle portion;
   conversion-means in said grip portion for converting a rotational movement generated from said motor into a reciprocal movement of said coupling means; and
   wherein said conversion means causes said coupling means to move reciprocally in a rotational direction around an axis of rotation of said coupling means.

5. An electrically driven toothbrush according to claim 4, wherein a tilting distance from an axis of rotation of said coupling means to a point in said bristle portion varies in response to the tilting movement of said bristle portion, and a reciprocating distance of said reciprocal movement of said bristle portion varies depending on said tilting distance.

6. An electrically driven toothbrush according to claim 4, further comprising:
   a battery accommodated in said grip portion;
   a grip conductor member coveting a surface of said grip portion and connected with one pole of said battery; and
   a second electrical conductor member on said grip portion connected with the other pole of said battery; and
   means for electrically connecting said bristles with said second electrical conductor member.

7. An electrically driven toothbrush according to claim 4, wherein said grip portion includes an outer casing, said casing comprising at least three cylindrical members connected together in a lengthwise direction of said grip portion, each of said cylindrical members being molded independently.

8. An electrically driven toothbrush comprising
a head portion including a bristle portion studded with bristles;
a grip portion adapted to be gripped manually and accommodating an electric motor and being a separate member from said head portion:
coupling means for detachably coupling said head portion to said grip portion, said coupling means supported on said grip portion in such a manner that said coupling means makes a reciprocal movement and having means for providing said head portion with a tilting motion relative to the grip portion; and
conversion means in said grip portion for converting a rotational movement, generated from said motor into a reciprocal movement of said coupling means wherein said conversion means causes said coupling means to move reciprocally in a rotational direction around an axis of rotation of said coupling means.

9. A toothbrush, comprising:
a head portion including a bristle portion at one end studded with bristles and a free portion at an opposite end;
a grip portion adapted to be gripped manually and being a separate member from said head portion;
a coupling means for detachably coupling said head portion to said grip portion, said coupling means having a connecting means pivotally connecting said free portion of said head portion to said coupling means at a distal end of said grip portion for providing said head portion with a tilting motion relative to the grip portion in response to pressure applied to said bristle portion; and
resilient means disposed within said coupling means against said free portion of said head portion for urging said connecting member in a direction such that said bristle portion of said pivotally connected head portion is urged in a direction toward teeth of a user.

10. An electrically driven toothbrush according to claim 9, further comprising:
a battery accommodated in said grip portion;
a grip electrical conductor member covering a surface of said grip portion and connected with one pole of said battery; and
a second electrical conductor member on said grip portion connected with the other pole of said battery; and
means for electrically connecting said bristles with said second electrical conductor member.

11. An electrically driven toothbrush to claim 10, wherein said grip conductor member is provided on a surface of at least one of said three cylindrical members.

12. An electrically driven toothbrush according to claim 10, wherein said second electrical conductor member comprises said pivotable connecting member.

* * * * *